US008247370B2

(12) United States Patent
Pelura

(10) Patent No.: US 8,247,370 B2
(45) Date of Patent: Aug. 21, 2012

(54) CONJOINT THERAPY FOR TREATING FIBROTIC DISEASES

(75) Inventor: Timothy J. Pelura, Malvern, PA (US)

(73) Assignee: Promedior, Inc., Malvern, PA (US)

( * ) Notice: Subject to any disclaimer, the term of this patent is extended or adjusted under 35 U.S.C. 154(b) by 315 days.

(21) Appl. No.: 12/448,035

(22) PCT Filed: Dec. 4, 2007

(86) PCT No.: PCT/US2007/024907
§ 371 (c)(1),
(2), (4) Date: Dec. 31, 2009

(87) PCT Pub. No.: WO2008/070117
PCT Pub. Date: Jun. 12, 2008

(65) Prior Publication Data
US 2010/0111898 A1 May 6, 2010

Related U.S. Application Data

(60) Provisional application No. 60/872,730, filed on Dec. 4, 2006.

(51) Int. Cl.
*A61K 39/00* (2006.01)
*A61K 39/395* (2006.01)
*A61K 38/00* (2006.01)

(52) U.S. Cl. ...................... 514/1.1; 424/130.1

(58) Field of Classification Search ........................ None
See application file for complete search history.

(56) References Cited

U.S. PATENT DOCUMENTS

| | | | |
|---|---|---|---|
| 4,233,969 A | 11/1980 | Lock et al. | |
| 4,782,014 A | 11/1988 | Serban et al. | |
| 5,092,876 A | 3/1992 | Dhawan et al. | |
| 5,591,709 A | 1/1997 | Lindenbaum | |
| 5,654,186 A | 8/1997 | Cerami et al. | |
| 5,698,589 A | 12/1997 | Allen | |
| 5,750,345 A | 5/1998 | Bowie | |
| 5,804,446 A | 9/1998 | Cerami et al. | |
| 5,846,796 A | 12/1998 | Cerami et al. | |
| 5,989,811 A | 11/1999 | Veltri et al. | |
| 6,037,458 A | 3/2000 | Hirai et al. | |
| 6,054,121 A | 4/2000 | Cerami et al. | |
| 6,071,517 A | 6/2000 | Fanger et al. | |
| 6,126,918 A | 10/2000 | Pepys et al. | |
| 6,174,526 B1 | 1/2001 | Cerami et al. | |
| 6,365,570 B1 | 4/2002 | Van Kessel et al. | |
| 6,406,698 B1 | 6/2002 | Svehang et al. | |
| 6,537,811 B1 | 3/2003 | Freier | |
| 6,600,019 B2 | 7/2003 | Prayaga et al. | |
| 6,660,843 B1 | 12/2003 | Feige et al. | |
| 6,872,541 B2 | 3/2005 | Mills | |
| 2002/0058284 A1 | 5/2002 | Winkel | |
| 2003/0003567 A1 | 1/2003 | Barber et al. | |
| 2003/0022245 A1 | 1/2003 | Mills | |
| 2003/0162180 A1 | 8/2003 | Pricop | |
| 2004/0068095 A1 | 4/2004 | Shimkets et al. | |
| 2004/0121343 A1 | 6/2004 | Buechler et al. | |
| 2005/0182042 A1* | 8/2005 | Feldman et al. | 514/211.07 |
| 2005/0238620 A1 | 10/2005 | Gomer et al. | |
| 2007/0048855 A1 | 3/2007 | Gamez et al. | |
| 2007/0065368 A1 | 3/2007 | Gomer et al. | |
| 2010/0317596 A1 | 12/2010 | Willett et al. | |

FOREIGN PATENT DOCUMENTS

| | | |
|---|---|---|
| WO | WO-92/21364 | 12/1992 |
| WO | WO 94/27640 | * 12/1994 |
| WO | WO-95/05394 | 2/1995 |
| WO | WO 95/33454 | * 12/1995 |
| WO | WO-97/26906 | 7/1997 |
| WO | WO-99/41285 | 8/1999 |
| WO | WO-01/74300 | 10/2001 |
| WO | WO-03/031572 | 4/2003 |
| WO | WO-03/097104 | 11/2003 |
| WO | WO-2004/016750 | 2/2004 |
| WO | WO-2004/058292 | 7/2004 |
| WO | WO-2004/059318 A2 | 7/2004 |
| WO | WO-2004/076486 | 9/2004 |
| WO | WO-2005/110474 | 11/2005 |
| WO | WO-2005/115452 | 12/2005 |
| WO | WO-2006/002438 | 1/2006 |
| WO | WO-2006/002930 | 1/2006 |
| WO | WO-2006/028956 | 3/2006 |
| WO | WO-2007/047207 | 4/2007 |
| WO | WO-2007/047796 | 4/2007 |
| WO | WO-2008/070117 | 6/2008 |
| WO | WO-2009/009034 | 1/2009 |

OTHER PUBLICATIONS

Chatziantoniou et al. (2008, Curr. Opin. Nephrol. Hypertension 17:76-81).*
Agostini et al. (2006, Proc. Am. Thorac. Soc. 3:357-363).*
Yu et al. (2002, Curr. Opin. Pharmacol. 2:177-181).*
Giri et al. (1997, Biochem. Pharmacol. 54:1205-1216).*
Wang et al. (2000, Biochem. Pharmacol. 60:1949-1958).*
Quan et al., "The role of circulating fibrocytes in fibrosis", Current Rheumatology Reports. 8(2): 145-150 (2006).
Sawada et al., "The Ace Inhibitor, Quinapril, Ameliorates Peritoneal Fibrosis in an Encapsulating Peritoneal Sclerosis Model in Mice", Pharmacological Research. 46(6): 505-510 (2002).
International Search Report, PCT/US2007/024907, dated Sep. 5, 2008.
Abe, R., et al., "Peripheral Blood Fibrocytes: Differentiation Pathway and Migration to Wound Sites," The Journal of Immunology, 166(12):7556-7562 (2001).
Aiba, S., et al., "Immunoglobulin-Producing Cells in Plasma Cell Orificial Mucositis," Journal of Cutaneous Pathology, 16(4):207-210 (1989).
Alles, V. V., et al., "Inducible expression of PTX3, a new member of the pentraxin family, in human mononuclear phagocytes," Blood, 84(10):3483-3493 (1994).

(Continued)

*Primary Examiner* — Elizabeth C Kemmerer
(74) *Attorney, Agent, or Firm* — Ropes & Gray LLP

(57) ABSTRACT

The present invention relates to improved methods of treating fibrotic or fibroproliferative disorders. Conjoint therapies are provided comprising the combination of one or more fibrocyte suppressors and one or more profibrotic factor antagonists or anti-fibrotic agents.

4 Claims, 1 Drawing Sheet

OTHER PUBLICATIONS

Ashcroft, T., et al., "Simple Method of Estimating Severity of Pulmonary Fibrosis on a Numerical Scale," J Clin Pathol, 41(4):467-470 (1988).

Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169(11):6490-6497 (2002).

Azuma, H., et al., "Superagonistic CD28 Antibody Induces Donor-Specific Tolerance in Rat Renal Allografts," American Journal of Transplantation, 8(10):2004-2014 (2008).

Bain, J., et al., "The Specificities of Protein Kinase Inhibitors: An Update," Biochem. J, 371(Pt 1):199-204 (2003).

Barna, B. P., et al., "Activation of Human Monocyte Tumoricidal Activity by C-Reactive Protein," Cancer Research, 47(5):3959-3963 (1987).

Bharadwaj, D., et al., "Serum Amyloid P Component Binds to Fcγ Receptors and Opsonizes Particles for Phagocytosis," The Journal of Immunology, 166(11):6735-6741 (2001).

Bharadwaj, D., et al., "The Major Receptor for C-Reactive Protein on Leukocytes Is Fcγ Receptor II," The Journal of Experimental Medicine, 190(4):585-590 (1999).

Bickerstaff, M. C. M., et al., "Serum Amyloid P Component Controls Chromatin Degradation and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Booth, DR., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," The Journal of Immunology, 166(7):4498-4506 (2001).

Castaño, A. P., et al., "Serum Amyloid P Inhibits Fibrosis Through FcγR-Dependent Monocyte-Macrophage Regulation in Vivo," Sci. Transl. Med. 1(5):1-26 (2009).

Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).

Chesney, J., et al., "Peripheral Blood Fibrocytes: Mesenchymal Precursor Cells and the Pathogenesis of Fibrosis," Curr. Rheumatology Reports, 2(6):501-505 (2000).

Chesney, J., et al., "Regulated Production of Type I Collagen and Inflammatory Cytokines by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRIIa on HL-60 Granulocytes," The Journal of Immunology, 168:1413-1418 (2002).

Christner, R. B., et al., "Binding of Human Serum Amyloid P-Component to Phosphocholine", Archives of Biochemistry and Biophysics, 314(2):337-343 (1994).

Clark, R. A. F., "Fibrin and Wound Healing," Annals New York Academy of Sciences 936:355-367 (2001).

Crouch, E., "Pathobiology of Pulmonary Fibrosis," Am J Physiol Lung Cell Mol Physiol, 259(4 Pt 1):L159-L184 (1990).

D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).

Daëron, M., "Fc Receptor Biology," Annual Review of Immunology 15:203-234 (1997).

Daëron, M., "Structural Bases of FcγR Functions," Int Rev Immunol. 16(1-2):1-27 (1997).

De Beer, F. C., et al., "Fibronectin and C4-Binding Protein are Selectively Bound by Aggregated Amyloid Component", J Exp Med., 154(4):1134-1149 (1981).

De Beer, F. C., et al., "Isolation and Characterization of C-Reactive Protein and Serum Amyloid P Component in the Rat," Immunology 45(1):55-70 (1982).

De Beer, F. C., et al., "Isolation of Human C-Reactive Protein and serum Amyloid P Component," Journal of Immunological Methods, 50(1):17-31 (1982).

de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).

De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.

Du Clos, T. W., "C-Reactive Protein Reacts With the U1 Small Nuclear Ribonucleoprotein," The Journal of Immunology, 143(8):2553-2559 (1989).

Du Clos, T. W., et al., "Reply to Human C-reactive protein does not bind to FcγRIIa on phagocytic cells," The Journal of Clinical Investigation, vol. 107(5):643 (2001).

Duchemin, A. M., et al., "Association of Non-Receptor Protein Tyrosine Kinases with the FcγRI/γ-Chain Complex in Monocytic Cells," The Journal of Immunology, 158(2):865-871 (1997).

Emsley, J., et al., "Structure of Pentameric Human Serum Amyloid P Component," Nature 367(6461):338-345 (1994).

Flesch, B. K., et al., "The FCGR2A-Arg131 Variant is no Major Mortality Factor in the Elderly—Evidence From a German Centenarian Study," International Journal of Immunogenetics, 33(4):277-279 (2006).

Garden, A. S., et al., "Head and Neck Radiation and Mucositis," 1(1):30-34 (2007).

Gerhard, et al., "The Status, Quality and Expansion of the NIH Full-Length cDNA Project: The Mammalian Gene Collection (MGC)," Genome Research, 14(10B):2121-2127 (2004).

Gewurz, H., et al., "Structure and Function of the Pentraxins," Current Opinion in Immunology, 7(1):54-64 (1995).

Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).

Giorgini, A., et al., "Blockade of Chronic Graft-Versus-Host Disease by Alloantigen-induced CD4+CD25+Foxp3+ Regulatory T Cells in Nonlymphopenic Hosts," Journal of Leukocyte Biology, 82(5):1053-1061 (2007).

Gregory, S. G., et al., "The DNA Sequence and Biological Annotation of Human Chromosome 1", Nature 441(7091):315-321 (2006).

Guyre, C. A., et al., "Receptor Modulation by FcγRI-Specific Fusion Proteins is Dependent on Receptor Number and Modified by IgG," The Journal of Immunology, 167(11):6303-6311 (2001).

Hamazaki, Hideaki, "Structure and significance of N-linked sugar unit of human serum amyloid P component," *Biochimica et Biophysica Acta*, 1037(3):435-438 (1990).

Harris, J. M., et al., "Pegylation A Novel Process for Modifying Pharmacokinetics," Clin. Pharmacokinetics, 40(7):539-551 (2001).

Hartlapp, I., et al., "Fibrocytes Induce an Angiogenic Phenotype in Cultured Endothelial Cells and Promote Angiogenesis in Vivo," The FASEB Journal, 5(12):2215-2224 (2001).

Heegaard, N. H. H., et al., "Ligand-Binding Sites in Human Serum Amyloid P Component," Eur. J. Biochem. 239(3):850-856 (1996).

Hicks et al., "Serum amyloid P component binds to histones and activates the classical complement pathway", The Journal of Immunology, 149:3689-3694 (1992).

Hind, C. R. K., et al., "Human Serum Amyloid P Component, a Circulating Lectin with Specificity for the Cyclic 4,6-Pyruvate Acetal of Galactose: Interactions with Various Bacteria", Biochem.J., 225(1):107-111 (1985).

Hind, C. R., et al, "Binding specificity of serum amyloid P-component for the pyruvate acetal of galactose," Journal of Experimental Medicine, 159(4):1058-1069 (1984).

Hohenester, E., et al., "Crystal Structure of a Decameric Complex of Human Serum Amyloid P Component with Bound dAMP", J. Mol. Biol. 269(4):570-578 (1997).

Huang, Z. Y., et al., "The Monocyte Fc$\gamma$ Receptors Fc$\gamma$RI/$\gamma$ and Fc$\gamma$RIIA Differ in their Interaction with Syk and with Src-Related Tyrosine Kinases," J Leukoc Biol 76(2):491-499 (2004).

Hundt, M., et al., "Treatment of Acute Exacerbation of Systemic Lupus Erythematosus with High-Dose Intravenous Immunoglobulin," Rheumatology (Oxford), 39(11):1301-1302 (2000).

Hutchinson, W. L., et al., "Human Serum Amyloid P Component is a Single Uncomplexed Pentamer in Whole Serum," Molecular Medicine, 6(6):482-493 (2000).

Janeway, et al., Immunobiology, 3rd edition, Garland Publishing, pp. 3:1-3:11 (1997).

Jenny, N. S., et al., "Serum Amyloid P and Cardiovascular Disease in Older Men and Women Results from the Cardiovascular Health Study," Arterioscler Thromb. Vasc. Biol., 27:352-358 (2007).

Junqueira, L. C., et al., "Picrosirius Straining Plus Polarization Microscopy, A Specific Method for Collagen Detection in Tissue Sections," Histochem. J, 11(4):447-455 (1975).

Kessel, A., et al., Intravenous Immunoglobulin Therapy Affects T Regulatory Cells by Increasing Their Suppressive Function, The Journal of Immunology, 179(8):5571-5575 (2007).

Kiernan, U. A., et al., "Proteomic Characterization of Novel Serum Amyloid P Component Variants from Human Plasma and Urine," Proteomics 4(6):1825-1829 (2004).

Kinoshita CM, et al., "A Protease-Sensitive Site in the Proposed Ca2+-Binding Region of Human Serum Amyloid Component and Other Pentraxins," Protein Sci., 1:700-709 (1992).

Kisseleva, T., et al., "Bone Marrow-Derived Fibrocytes Participate in Pathogenesis of Liver Fibrosis," Journal of Hepatology, 45(3):429-438 (2006).

Kivela-Rajamaki, M. J., et al., "Laminin-5-$\gamma$2-chain and collagenase-2 (MMP-8) in Human Peri-Implant Sulcular Fluid," Clin. Oral Implants Res., 14(2):158-165 (2003).

Kolstoe et al., "Molecular dissection of Alzheimer's disease neuropathology by depletion of serum amyloid P component", PNAS, 106(18):7619-7623 (2009).

Korade-Mirnics, Z., et al., "Src Kinase-Mediated Signaling in Leukocytes," J Leukoc Biol., 68(5):603-613 (2003).

Kucuk, H. F., et al., "Effect of a Selective Cyclooxygenase-2 Inhibitor on Renal Scarring," European Surgical Research, 38(5):451-457 (2006).

Lai, J. Y., et al., "Potent Small Molecule Inhibitors of Spleen Tyrosine Kinase (Syk)," Bioorganic & Medicinal Chemistry Letters, 13(18):3111-3114 (2003).

Lei, K. K., et al., "Genomic DNA Sequence for Human C-Reactive Protein," J. Biol. Chem. 260(24):13377-13383 (1985).

Lindenbaum, E. S., et al., "Serum-Free Cell Culture Medium Induces Acceleration of Wound Healing in Guinea-Pigs," Burns, 21(2):110-115 (1995).

Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).

Lu, J., et al., "Structural Recognition and Functional Activation of Fc$\gamma$R by Innate Pentraxins," Nature, 456(7224):989-992 (2008).

Majno, G., "Chronic Inflammation: Links With Angiogenesis and Wound Healing," American Journal of Pathology, 153(4):1035-1039 (1998).

Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).

Marnell, L. L., et al., "C- Reactive Protein Binds to Fc$\gamma$RI in Transfected COS Cells," The Journal of Immunology, 155(4):2185-193 (1995).

Metz, C. N., "Fibrocytes: A Unique Cell Population Implicated in Wound Healing," Cell. Mol. Life Sci., 60(7):1342-1350 (2003).

Mold, C., et al., "Serum Amyloid P Component and C-Reactive Protein Mediate Phagocytosis Through Murine Fc$\gamma$Rs," The Journal of Immunology, 166(2):1200-1205 (2001).

Moore, B. B., et al., "CCR2-Mediated Recruitment of Fibrocytes to the Alveolar Space After Fibrotic Injury," American Journal of Pathology, 166(3):675-684 (2005).

Mori, L., et al., "Fibrocytes Contribute to the Myofibroblast Population in Wounded Skin and Originate From the Bone Marrow," Exp Cell Res., 304(1):81-90 (2005).

Mortensen, R. F., et al., "Regulation of phagocytic leukocyte activities by C-reactive protein," Journal of Leukocyte Biology, 67(4):495-500 (2000).

Murphy, T. M., et al., "Extrahepatic Transcription of Human C-Reactive Protein," Journal of Experimental Medicine, 73(2):495-498 (1991).

Murray, L. A., et al., "Serum Amyloid P Therapeutically Attenuates Murine Bleomycin-induced Pulmonary Fibrosis Via Its Effects on macrophages," PLoS, 5(3):e9683 (2010).

Ohnishi, S. et al., "Isolation and Characterization of the Complete Complementary and Genomic DNA Sequences of Human Serum Amyloid P Component," J. Biochem, 100(4):849-858 (1986).

Oliveira, E. B., et al., "Primary Structure of Human C-Reactive Protein," The Journal of Biological Chemistry, 254(2):489-502 (1979).

Oriente, A., et al., "Interleukin-13 Modulates Collagen Homeostasis in Human Skin and Keloid Fibroblasts," The Journal of Pharmacology and Experimental Therapeutics, 292(3):988-994 (2000).

Osmand, A. P., et al., "Partial Amino-Acid Sequences of Human and Rabbit C-Reactive Proteins: Homology with Immunoglobulins and Histocompatibility Antigens," Proc. Natl. Acad. Sci. U.S.A., 74(3):1214-1218 (1977).

Pachence, J., et al., "Tissue-Activated Delivery—Novel Methods for Site-Directed Drug Delivery," Drug Delivery Technology, 3(1):40-45 (2003).

Painter, R. H., "Evidence that Clt (Amyloid P-component) is not a subcomponent of the first component of complement (CI);" J. Immunol., 119(6):2203-2205 (1977).

Paul, William E., M.D., editor, Fundamental Immunology, 3d ed. Raven Press, p. 242 (1993).

Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998).

Pepys et al., Glycobiology of Human Serum Amyloid P Component Amyloid Amyloidosis, Proc. Int. Symp. Amyloidosis, pp. 177-179 (1994).

Pepys, et al., "Targeted pharmacological depletion of serum amyloid P component for treatment of human amyloidosis", Nature, 471:254-259 (2002).

Pepys, et al., Human serum amyloid P component is an invariant constituent of amyloid deposits and has a uniquely homogeneous glycostructure, PNAS, 91:5206-5606 (1994).

Pepys, M. B., "Isolation of serum amyloid P-component (Protein SAP) in the Mouse," Immunology, 37(3):637-641 (1979).

Pepys, M. B., et al., "Amyloid P Component. A Critical Review," Amyloid: Int. J. Exp. Invest., 4(4):274-295 (1997).

Pepys, M. B., et al., "Serum Amyloid P Component is the Major Calcium-Dependent Specific DNA Binding Protein of Serum," Biochemical and Biophysical Research Communications, 148(1):308-313 (1987).

Philips, R. J., et al., "Circulating Fibrocytes Traffic to the Lungs in Response to CXCL 12 and Mediate Fibrosis," The Journal of Clinical Investigation, 114(3):438-446 (2004).

Pilling, D. et al., "Inhibition of Fibrocyte Differentiation by Serum Amyloid P," The Journal of Immunology, 17(10):5537-5546 (2003).
Pilling, D., et al., "Aggregated IgG Inhibits the Differentiation of Human Fibrocytes," Journal of Leukocyte Biology, 7996:1242-1251 (2006).
Pilling, D., et al., "Reduction of Bleomycin-Induced Pulmonary Fibrosis by Serum Amyloid P," The Journal of Immunology, 179(6):4035-4044 (2007).
Pontet, M., et al., "One step preparation of both human C-reactive protein and Cit," FEBS Letters, 88(2):172-175 (1978).
Portolano et al., "Lack of Promiscuity in Autoantigen-Specific H and L Chain Combinations as Revealed by Human H and L Chain "Roulette","J. Immunol., 150(3):880-887, 1993.
Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).
Prelli, F., et al., "The Primary Structure of Human Tissue Amyloid P Component From a Patient with Primary Idiopathic Amyloidosis," The Journal of Biological Chemistry, 260(24):12895-12898 (1985).
Rudikoff et al., "Single amino acid substitution altering antigen-binding specificity," Proc Natl Acad Sci USA, 79(6):1979-1983 (1982).
Russo, F. P., et al., "Liver Fibrosis; Bone Marrow Functionality Contributes to Liver Fibrosis," Gastroenterology Week Jul. 31, 2006, 130(6):83-84.
Sada, K., et al., "Structure and Function of Syk Protein-Tyrosine Kinase," J Biochem, 130(2):177-186 (2001).
Saeland, E., et al., "Human C-reactive Protein Does not Bind to FcγRIIa on Phagocytic Cells," The Journal of Clinical Investigation, 107(5):641-643 (2001).
Schmidt, M., et al., "Identification of Circulating Fibrocytes as Precursors of Bronchial Myofibroblasts in Asthma," The Journal of Immunology, 171(1):380-389 (2003).
Shoenfeld, Y., et al., "The mosaic of Autoimmunity: Prediction, Autoantibodies, and Therapy in Autoimmune Diseases—2008," Israel Medical Association Journal, 10(1):13-19 (2008).
Shrive, A. K., et al., "Three Dimensional Structure of Human C-Reactive Protein," Nature Structural Biology, 3(4):346-354 (1996).
Siebert et al., "Effect of enzymatic desialylation of human serum amyloid P component on surface exposure of laser photo CIDNP (chemically induced dynamic nuclear polarization)—reactive histidine, tryptophan and tyrosine residues," *FEBS Letters*, 371(1):13-6 (1995).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRIIa on Human Monocytes and Neutrophils is Allele-Specific," The Journal of Clinical Investigation, 105(3):369-376 (2000).
Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).

Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).
Toubi, E., et al., "High Dose Intravenous Immunoglobulins: An Option in the Treatment of Systemic Lupus Erythematosus," Human Immunology, 66(4):395-402 (2005).
Tridandapani, S., et al., "Regulated Expression and Inhibitory Function of Fcγ-RIIb in Human Monocytic Cells," Journal of Biological Chemistry, The American Society for Biochemistry and Molecular Biology, Inc, 277(7):5082-5089 (2002).
Trinchieri, G., "Interleukin-12 and the Regulation of Innate Resistance and Adaptive Immunity," Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).
Turner, M., et al., "Tyrosine Kinase SYK: Essential Functions for Immunoreceptor Signalling," Immunology Today, 21(3):148-154 (2000).
Underwood, D. C., et al., "SB 239063, a p38 MAPK Inhibitor, reduces Neutrophilia, Inflammatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yang, L., et al., "Identification of Fibrocytes in Postburn Hypertrophic Scar," Wound Repair and Regeneration, 13(4):398-404 (2005).
Zahedi K., "Characterization of the Binding of Serum Amyloid P to Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).

* cited by examiner

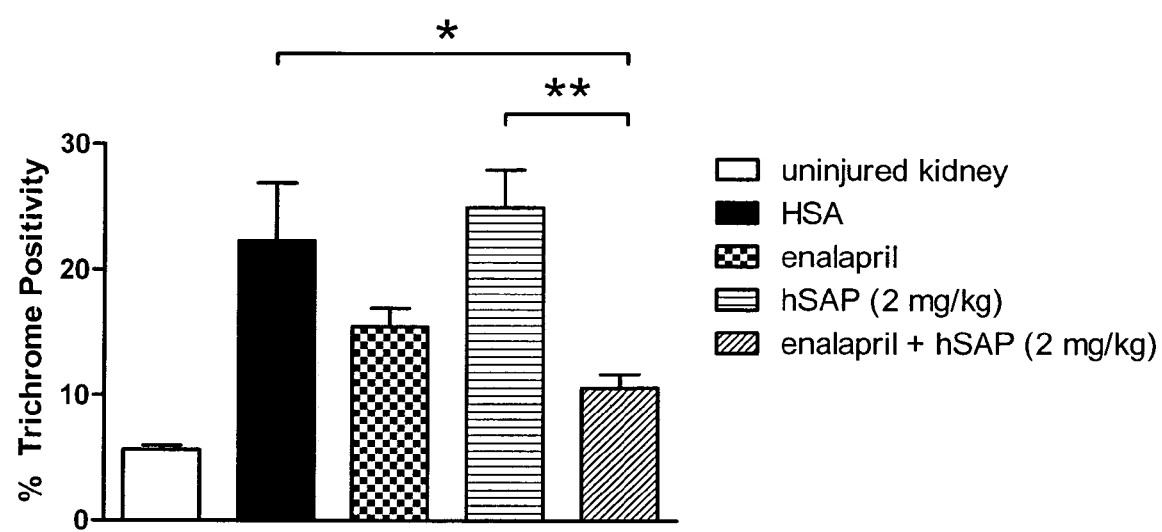

CONJOINT THERAPY FOR TREATING FIBROTIC DISEASES

RELATED APPLICATIONS

This application is a national stage filing under 35 U.S.C. 371 of International Application No. PCT/US2007/024907, filed on Dec. 4, 2007, which claims the benefit of the filing date of U.S. Provisional Application No. 60/872,730, filed on Dec. 4, 2006. The teachings of the referenced Applications are incorporated herein by reference in their entirety. International Application No. PCT/US2007/024907 was published under PCT Article 21(2) in English.

BACKGROUND OF THE INVENTION

The process of tissue repair as a part of wound healing involves two phases. The first phase is the regenerative phase, in which injured cells are replaced by cells of the same type.

The second phase is the formation of fibrous tissues, also called fibroplasia or fibrosis, in which connective tissue replaces normal parenchymal tissues. The tissue repair process can become pathogenic if the fibrosis phase continues unchecked, leading to extensive tissue remodeling and the formation of permanent scar tissue.

It has been estimated that up to 45% of deaths in the United States can be attributed to fibroproliferative diseases, which can affect many tissues and organ systems. Major organ fibrotic diseases include interstitial lung disease (ILD), characterized by pulmonary inflammation and fibrosis. ILD is known to have a number of causes such as sarcoidosis, silicosis, collagen vascular diseases, and systemic scleroderma. However, idiopathic pulmonary fibrosis, a common type of ILD, has no known cause. Other organ fibrotic disorders include liver cirrhosis, liver fibrosis resulting from chronic hepatitis B or C infection, kidney disease, heart disease, and eye diseases including macular degeneration and retinal and vitreal retinopathy. Fibroproliferative disorders also include systemic and local scleroderma, keloids and hypertrophic scars, atherosclerosis, and restenosis. Additional fibroproliferative diseases include excessive scarring resulting from surgery, chemotherapeutic drug-induced fibrosis, radiation-induced fibrosis, and injuries and burns.

Currently, treatments are available for fibrotic disorders including general immunosuppressive drugs such as corticosteroids, and other anti-inflammatory treatments. However, the mechanisms involved in regulation of fibrosis appear to be distinctive from those of inflammation, and anti-inflammatory therapies are not always effective in reducing or preventing fibrosis. Therefore, a need remains for developing treatments to reduce and prevent fibrosis and control fibrotic disorders.

Wound healing and the disregulated events leading to fibrosis both involve the proliferation and differentiation of fibroblasts and the deposition of extracellular matrix. Whether these fibroblasts are locally derived or from a circulating precursor population is unclear. Fibrocytes are a distinct population of fibroblast-like cells derived from peripheral blood monocytes that enter sites of tissue injury to promote angiogenesis and wound healing. Recently, it has been reported that CD14-[+] peripheral blood monocytes cultured in the absence of serum or plasma differentiate into fibrocytes within 72 hours, but that serum amyloid P (SAP) was able to inhibit fibrocyte differentiation at levels similar to those found in plasma. In contrast, depleting SAP reduces the ability of plasma to inhibit fibrocyte differentiation. Compared with sera from healthy individuals and patients with rheumatoid arthritis, sera from patients with scleroderma and mixed connective tissue disease, two systemic fibrotic diseases, were less able to inhibit fibrocyte differentiation in vitro and had correspondingly lower serum levels of SAP. These results suggest that low levels of SAP may thus augment pathological processes leading to fibrosis. These data also suggest mechanisms to inhibit fibrosis in chronic inflammatory conditions, or conversely to promote wound healing.

As SAP binds to Fc receptors for immunoglobulin G (IgG; FcRs), FcR activation was subsequently demonstrated to be an inhibitory signal for fibrocyte differentiation. FcR are activated by aggregated IgG, and it has been shown that aggregated but not monomeric, human IgG inhibits human fibrocyte differentiation. Monoclonal antibodies that bind to FcRI (CD64) or FcRII (CD32) also inhibit fibrocyte differentiation. Aggregated IgG lacking Fc domains or aggregated IgA, IgE, or IgM do not inhibit fibrocyte differentiation. Incubation of monocytes with aggregated IgG, like SAP, inhibited fibrocyte differentiation. Using inhibitors of protein kinase enzymes, it has also been shown that Syk- and Src-related tyrosine kinases participate in the inhibition of fibrocyte differentiation. These observations suggest that fibrocyte differentiation can occur in situations where SAP and aggregated IgG levels are low, such as the resolution phase of inflammation.

BRIEF SUMMARY OF THE INVENTION

The present invention relates to the use of conjoint therapies for treating fibrotic and fibroproliferative disorders, involving administering a combination of agents that suppress fibrocyte formation ("fibrocyte suppressors") with agents that inhibit activation of resident collagen producing cells such as fibroblasts, myofibroblasts, or myofibrocytes, such as antagonist of TGF-β and other profibrotic factors (collectively "profibrotic factor antagonists").

In certain embodiments, the subject method and compositions can be practiced using such fibrocyte suppressors as serum amyloid P (SAP), IL-12, Laminin-1, anti-FcγR antibodies that are able to cross-link FcγR, aggregated IgG, cross-linked IgG and/or combinations thereof. Designations for "SAP", "IL-12", "Laminin-1", IgG and anti-FcγR antibodies as used herein also refer to functional fragments of these proteins unless it is clear that such fragments are excluded from the usage in a given context. In certain embodiments, the fibrocyte suppressor is an agent that induces apoptosis of monocytes, such as an IL-15 antagonist.

In certain embodiments, the profibrotic factor antagonists are selected from antagonists of peptide growth factors, cytokines, chemokines, and the like. Examples of such factors that may be antagonized by the subject profibrotic factor antagonists include to transforming growth factor type beta (TGF-β), VEGF, EGF, PDGF, IGF, RANTES, members of the interleukin family (e.g., IL-1, IL-4, IL-5, IL-6, IL-8 and IL-13), tumor necrosis factor type alpha (TNF-α), platelet-derived growth factor (PDGF), basic fibroblast growth factor (bFGF), monocyte chemoattractant protein type 1 (MCP-1), macrophage inflammatory protein (e.g., MIP-1α, MIP-2), connective tissue growth factor (CTGF), endothelin-1, angiotensin-II, leptin, chemokines (e.g., CCL2, CCL12, CXCL12, CXCR4, CCR3, CCR5, CCR7, SLC/CCL21), integrins (e.g., α1β1, α2β1, αvβ6, αvβ3), tissue inhibitors of matrix metalloproteinases (e.g., TIMP-1, TIMP-2) and other factors known to promote or be related to the formation, growth, or maintenance of fibrotic tissue.

In certain embodiments, the profibrotic factor antagonists can be replaced with, or augmented with, a cytokine known to have anti-fibrotic effects itself, such as IFN-γ, BMP-7, HGF or IL-10.

Such components of the combined treatment may be administered to a target location as part of a single formulation, in which the single formulation includes components for targeting both events. In other selected embodiments of the present invention, the components may be administered as separate formulations.

A decrease in or suppression of both differentiation of fibrocytes and the formation and maintenance of fibrotic tissue may alleviate symptoms of numerous fibrosing diseases or other disorders caused by fibrosis. For example, it may be used to treat fibrosis in the liver, kidney, lung, heart and pericardium, eye, skin, mouth, pancreas, gastrointestinal tract, brain, breast, bone marrow, bone, genitourinary, a tumor, or a wound.

The present invention provides methods for modulating fibroblast accumulation and collagen deposition in a tissue.

DETAILED DESCRIPTION OF THE DRAWINGS

FIG. 1 depicts the extent of Trichrome staining in a rat kidney unilateral ureter obstruction (UUO) injury model.

DETAILED DESCRIPTION OF CERTAIN EMBODIMENTS

I. Overview

The regulation of events leading to fibrosis involves at least two major events. One is the proliferation and differentiation of fibrocytes. Fibrocytes are a distinct population of fibroblast-like cells derived from peripheral blood monocytes that normally enter sites of tissue injury to promote angiogenesis and wound healing. Fibrocytes differentiate from CD14+ peripheral blood monocytes, and may differentiate from other PBMC cells. The presence of SAP, IL-12, Laminin-1, anti-FcγR antibodies, crosslinked IgG and/or aggregated IgG may inhibit or at least partially delay this process.

The second major event is the formation and maintenance of fibrotic tissue. Fibrotic tissue may be formed and maintained by the recruitment and proliferation of fibroblast cells, the formation of new extracellular matrix, and the growth of new vascular tissue. In pathologic fibrosis, such as following chronic inflammation, injury, or idiopathic fibrosis, it is this excess fibrotic tissue that can lead to tissue damage and destruction.

Since both of the foregoing events are necessary for fibrosis, treatments of the present invention include combined compositions and methods in which both of these events are targeted. In selected embodiments, the present invention include at least one composition, or administration thereof to a target location, that is suitable for the inhibition or delay of fibrocyte differentiation, and at least one component, or administration thereof to the target location, that is suitable for the inhibition or antagonizing of profibrotic factors. In selected embodiments, these components may be formulated or administered as a combined composition, or may separately and/or independently administered to the target locations.

The present invention provides methods for treating fibrotic and fibroproliferative disorders. The method generally involves administering an effective amount of a fibrocyte suppressor in combination with an effective amount of profibrotic factor antagonist. The methods provide for treatment of fibrotic diseases, including those affecting the lung, liver, heart, kidney and eye. To further illustrate, the subject method can be used to treat such fibroproliferative diseases as glomerulonephritis (GN); diabetic nephropathy; renal interstitial fibrosis; renal fibrosis resulting from complications of drug exposure; HIV-associated nephropathy; transplant necropathy; liver cirrhosis due to all etiologies; disorders of the biliary tree; hepatic dysfunction attributable to infections; pulmonary fibrosis; adult respiratory distress syndrome (ARDS); chronic obstructive pulmonary disease (COPD); idiopathic pulmonary fibrosis (IPF); acute lung injury (ALI); pulmonary fibrosis due to infectious or toxic agents; congestive heart failure; dilated cardiomyopathy; myocarditis; vascular stenosis; progressive systemic sclerosis; polymyositis; scleroderma; Grave's disease; dermatomyositis; fascists; Raynaud's syndrome, rheumatoid arthritis; proliferative vitreoretinopathy; fibrosis associated with ocular surgery; acute macular degeneration, and excessive or hypertrophic scar or keloid formation in the dermis occurring during wound healing resulting from trauma or surgical wounds. Still other exemplary fibrotic disorders that can be treated with the subject conjoint therapy are described in further detail below. The etiology may be due to any acute or chronic insult including toxic, metabolic, genetic and infectious agents.

In some embodiments, an effective amount of fibrocyte suppressor and an effective amount of profibrotic factor antagonist are amounts that, when administered in combination therapy, are effective to reduce fibrosis by at least about 10%, and more preferably at least about 15%, 20%, 25%, 30%, 35%, 40%, 45%, or even at least about 50%, or more, compared with the degree of fibrosis in the individual prior to treatment with the combination therapy.

In other embodiments, the present invention provides methods that involve administering a synergistic combination of fibrocyte suppressor and profibrotic cytokine antagonist. As used herein, a "synergistic combination" of fibrocyte suppressor and profibrotic cytokine antagonist is a combined dosage that is more effective in the therapeutic or prophylactic treatment than the incremental improvement in treatment outcome that could be predicted or expected from a merely additive combination of (i) the therapeutic or prophylactic benefit of a fibrocyte suppressor when administered at that same dosage as a monotherapy and (ii) the therapeutic or prophylactic benefit of the profibrotic cytokine antagonist when administered at the same dosage as a monotherapy.

II. Definitions

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a fibrotic or fibroproliferative disorder and/or adverse affect attributable to the disorder. "Treatment", as used herein, covers any treatment of a disease in a mammal, particularly in a human, and includes: (a) increasing-survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein the term "subject" refers to animals including mammals including humans. The term "mammal" includes primates, domesticated animals including dogs, cats, sheep, cattle, goats, pigs, mice, rats, rabbits, guinea pigs, captive animals such as zoo animals, and wild animals. As used herein the term "tissue" refers to an organ or set of specialized cells such as skin tissue, lung tissue, kidney tissue, and other types of cells.

The term "therapeutically effective amount" is meant an amount of a fibrocyte suppressor or profibrotic factor antagonist, or a rate of delivery of such therapeutic agents, effective to facilitate a desired therapeutic effect. The precise desired therapeutic effect will vary according to the fibrotic or fibroproliferative condition to be treated, the formulation to be administered, and a variety of other factors that are appreciated by those of ordinary skill in the art.

As used herein the terms "fibroproliferative disorder" and "fibrotic disorder" refer to conditions involving fibrosis in one or more tissues. As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. As used herein the term "fibrosis" is used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called α-chains, which are wound around each other in a ropelike helix. Collagen exists in several forms or types; of these, type I, the most common, is found in skin, tendon, and bone; and type III is found in skin, blood vessels, and internal organs.

Fibrotic disorders include, but are not limited to, systemic and local scleroderma, keloids and hypertrophic scars, atherosclerosis, restinosis, pulmonary inflammation and fibrosis, idiopathic pulmonary fibrosis, liver cirrhosis, fibrosis as a result of chronic hepatitis B or C infection, kidney disease, heart disease resulting from scar tissue, and eye diseases such as macular degeneration, and retinal and vitreal retinopathy. Additional fibrotic diseases include fibrosis resulting from chemotherapeutic drugs, radiation-induced fibrosis, and injuries and burns.

"Scleroderma" is a fibrotic disorder characterized by a thickening and induration of the skin caused by the overproduction of new collagen by fibroblasts in skin and other organs. Scleroderma may occur as a local or systemic disease. Systemic scleroderma may affect a number of organs. Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. Pulmonary fibrosis affects 30 to 70% of scleroderma patients, often resulting in restrictive lung disease.

"Idiopathic pulmonary fibrosis" is a chronic, progressive and usually lethal lung disorder, thought to be a consequence of a chronic inflammatory process.

As used herein the term "profibrotic factors" refers to cytokines, growth factors or chemokines which have been observed to promote the accumulation of fibroblasts and deposition of collagen in various tissues. A number of cytokines and growth factors have been reported to be involved in regulating tissue remodeling and fibrosis. These include the "profibrotic cytokines" such as transforming growth factor beta (TGF-β), interleukin-4 (IL-4), interleukin-5 (IL-5), and interleukin-13 (IL-13), which have been shown to stimulate collagen synthesis and fibrosis in fibrotic tissues (Letterio et al. *Ann Rev. Immunol.* 16, 137-161 (1998), Fertin et al., *Cell Mol. Biol.* 37, 823-829 (1991), Doucet et al., *J. Clin. Invest.* 101, 2129-2139 (1998). Interleukin-9 (IL-9) has been shown to induce airway fibrosis in the lungs of mice (Zhu et al., *J. Clin. Invest.* 103, 779-788 (1999)). In addition to TGF-β, other cytokines or growth factors which have been reported to increase fibrosis in the fibrotic disorder idiopathic pulmonary fibrosis (IPF) include granulocyte/macrophage-colony stimulating factor (GM-CSF), tumor necrosis factor alpha (TNF-α), interleukin-1 beta (IL-1β), and connective tissue growth factor (CTGF) (Kelly et al. *Curr Pharmaceutical Des* 9: 39-49 (2003)). Cytokines and growth factors reported to be involved in promoting pulmonary fibrosis occurring in scleroderma include TGF-β, interleukin-1 beta (IL-1β), interleukin-6 (IL-6), oncostatin M (OSM), platelet derived growth factor (PDGF), the type 2 cytokines IL-4 and IL-13, IL-9, monocyte chemotactic protein 1 (CCL2/MCP-1), and pulmonary and activation-regulated chemokine (CCL18/PARC) (Atamas et al., *Cyto Growth Fact Rev* 14: 537-550 (2003)).

As used herein, the terms "antibody" and "antibodies" refer to monoclonal antibodies, multispecific antibodies, human antibodies, humanized antibodies, synthetic antibodies, chimeric antibodies, camelized antibodies, single-chain antibodies or single-chain Fvs (scFv), Fab fragments, F(ab') fragments, disulfide-linked Fvs (sdFv), and intrabodies. In addition, unless otherwise indicated (such as in the case of aggregated IgG), the term includes epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class or subclass.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. In specific embodiments, scFvs include humanized scFvs.

As used herein, the term "humanized antibody" refers to forms of non-human (e.g., murine) antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody may comprise at least a portion of an immunoglobulin constant region (Fc) that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

III. Exemplary Embodiments

A. Suppressors of Fibrocyte Proliferation and Differentiation

One component of the conjoint therapies of the instant invention are agents that suppress fibrocyte formation. These fibrocyte suppressors, as they are generically referred to herein, are agents that may act on CD14[+] peripheral blood monocytes in a manner that either suppresses the formation of fibrocytes (e.g., inhibits differentiation or proliferation), or in other embodiments, causes the ablation (cell death) of the monocytes.

In certain embodiments, the fibrocyte suppressor is an agent that causes FcγR-dependent activation of Syk- and Src-related tyrosine kinases in monocytes. In other embodiments, the fibrocyte suppresser can be an agent that works downstream of the FcγR complex, causing FcγR-independent activation of a Syk- and Src-related tyrosine kinase in monocytes in a manner that suppresses fibrocyte formation. Various small molecule activators of the syk-kinase, such as phospho-ITAM peptides and peptidomimetics thereof, may be useful for this purpose.

Other exemplary fibrocyte suppressors include:
(i) Serum Amyloid P

It has been previously identified that fibrocytes may differentiate from CD14+ peripheral blood monocytes, and the presence of human serum dramatically delays this process. The factor in human serum that inhibits fibrocyte differentiation is serum amyloid P (SAP). SAP, a member of the pentraxin family of proteins that includes C-reactive protein (CRP), is produced by the liver, secreted into the blood, and circulates in the blood as stable pentamers. SAP binds to receptors for the Fc portion of IgG antibodies (FcγR) on a variety of cells and may effectively cross-link FcγR without additional proteins because SAP is a pentameric protein with five potential FcγR binding sites per molecule. As SAP binds to FcγR, intracellular signaling events consistent with FcγR activation are initiated.

In specific embodiments of the present invention, compositions containing SAP may be operable to raise SAP concentration in target locations to approximately at least 0.5 μg/ml. In humans, $I^{125}$ radiolabelled SAP has been previously administered to study patients with amyloidosis. In the treatments, approximately 600 μg of SAP was administered to an adult human. Accordingly, administration of approximately 600 μs of SAP systemically to an adult human is safe. Higher dosages may also be safe under appropriate conditions.

SAP supplied in certain compositions of the present invention may include the entire SAP protein or a portion thereof, preferably the portion functional in suppression of fibrocyte formation. In one embodiment, the functional portion of SAP is selected from the region that does not share sequence homology with CRP, which has no effect on fibrocyte formation. For instance amino acids 65-89 (KERVGEYSLYIGRH-KVTPKVIEKFP-SEQ.ID.NO.1) of SAP are not homologous to CRP. Amino acids 170-181 (ILSAYAYQGTPLPA-SEQ.ID.NO.2) and 192-205 (IRGYVIIKPLV-SEQ.ID.NO.3) are also not homologous. Additionally a number of single amino acid differences between the two proteins are known and may result in functional differences.

(ii) IL-12

IL-12 has been previously implicated in fibrosis and fibrosing diseases, but most studies have focused on the role of IL-12 in promoting the Th1 immune response or by triggering the production of interferon-γ.

Compositions containing IL-12 may be operable to raise the IL-12 concentration in target locations to approximately 0.1 to 10 ng/ml.

(iii) Laminin-1

Laminins are extracellular matrix proteins involved in movement of monocytes from the circulation into tissues. In order for leukocytes to enter tissues, they must cross through endothelial cells and the surrounding basement membrane of blood vessel wall. This process involves the tethering, rolling and stopping of the leukocytes on the endothelial cells. Following adhesion to the endothelial cells, leukocytes then cross between the endothelial cells, through the blood vessel wall and into the tissues. The process of extravasation of cells through blood vessel walls alters their phenotype and function.

These events are controlled by a series of cell surface adhesion receptors, including integrins. Integrins bind to a wide variety of ligands, including extracellular matrix proteins to (ECM), such as fibronectin, vitronectin, collagen and laminin. Matrix proteins are present within the basement of the blood vessel wall, including laminins. Laminins are a large family of glycoproteins, with a heterotrimeric structure of α, β and γ chains. The use of different α, β and γ chains leads to the expression of at least 12 different laminin isoforms. Different laminins are expressed at different stages of development and at different sites within the body.

Compositions containing Laminin-1 may be operable to raise the Laminin-1 concentration in target locations to approximately 1 to 10 μg/ml.

(iv) Anti-FcγR Antibodies

It has also been identified that Anti-FcγR antibodies may prevent the differentiation of peripheral blood monocytes into fibrocytes. Anti-FcγR antibodies are IgG antibodies that bind to receptors for the Fc portion of IgG antibodies (FcγR). The anti-FcγR antibodies bind through their variable region, and not through their constant (Fc) region. However, IgG from the appropriate source (e.g. human IgG for human receptors) may normally bind to FcγR through its Fc region. FcγR are found on the surface of a variety of hematopoietic cells. There are four distinct classes of FcγR. FcγRI (CD64) is expressed by peripheral blood monocytes and binds monomeric IgG with a high affinity. FcγRII (CD32) and FcγRIII (CD16) are low affinity receptors for IgG and only efficiently bind aggregated IgG. FcγRII is expressed by peripheral blood B cells and monocytes, whereas FcγRIII is expressed by NK cells and a subpopulation of monocytes. FcγRIV was recently identified in mice and is present on murine peripheral blood monocytes and neutrophils, macrophages and dendritic cells and efficiently binds murine IgG2a and IgG2b antibodies. There is a putative human FcγRIV gene, but the biological function of the protein, such as ligand specificity and cellular expression is, as yet unknown.

Peripheral blood monocytes express both FcγRI and FcγRII (a subpopulation of monocytes express FcγRIII), whereas tissue macrophages express all three classical FcγR. Clustering of FcγR on monocytes by IgG, either bound to pathogens or as part of an immune complex, initiates a wide variety of biochemical events.

FcγR activation and induction of intracellular signaling pathways may occur when multiple FcγR are cross-linked or aggregated. This FcγR activation leads to a cascade of signaling events initiated by two main kinases. The initial events following FcγR activation to involve the phosphorylation of intracellular immunoreceptor tyrosine activation motifs (ITAMs) present on the cytoplasmic tail of FcγRII or the FcR-γ chain associated with FcγRI and FcγRIII, by Src-related tyrosine kinases (SRTK). In monocytes, the main Src-kinases associated with FcγRI and FcγRII are hck and lyn. The phosphorylated ITAM then recruit cytoplasmic SH2-containing kinases, especially Syk, to the ITAMs and Syk then activates a series of downstream signaling molecules.

Anti-FcγR antibodies for FcγRI (anti-FcγRI) and for FcγRII (anti-FcγRII) are able to bind to either FcγRI or FcγRII, respectively. These FcγR may then be cross-linked by the binding of additional antibodies or other means. This process initiates intracellular signaling events consistent with FcγR activation.

Compositions containing anti-FcγRI antibodies and/or anti-FcγRII antibodies, and/or cross-linked or aggregated IgG, which may bind to FcγR through the Fc region, may be used to suppress the differentiation of fibrocytes in inappropriate locations and in fibrosing disorders and chronic inflammatory conditions, inter alia.

In specific embodiments, compositions containing approximately 1 μg/ml anti-FcγR antibodies may be effective to inhibit fibrocyte differentiation by approximately 50%. In other embodiments, compositions may contain an amount sufficient to deliver 1 μg/ml anti-FcγR antibodies to the target tissue. In other specific embodiments, compositions may contain as little as 0.1 μg ml cross-linked or aggregated IgG.

Anti-FcγR antibodies may be administered in a dose of approximately 1.0 μg/mL, in an amount sufficient to deliver 1 μg/ml anti-FcγR antibodies to the target tissue, or in another dose sufficient to inhibit fibrocyte differentiation without causing an undesirable amount of cell death in the patient. Aggregated or cross-linked IgG may be administered in an amount sufficient to deliver at least 0.1 μg/ml IgG to the target tissue, or in another dose sufficient to inhibit fibrocyte differentiation without causing an undesirable amount of cell death in the patient.

Anti-FcγR antibodies used in examples of the present disclosure include anti-FcγRI antibodies and anti-FcγRII antibodies.

Anti-FcγR antibodies may include any isotype of antibody.

(v) Aggregated Fc Domains and Fc-Containing Antibodies

Cross-linked or aggregated IgG may include any IgG able to bind the target FcγR through its Fc region, provided that at least two such IgG antibodies are physically connected to one another.

Antibodies of both types may include whole antibodies or a portion thereof, preferably the portion functional in suppression of fibrocyte differentiation. For example, they may include any antibody portion able to cross-link FcγR. This may include aggregated or cross-linked antibodies or fragments thereof, such as aggregated or cross-linked whole antibodies, $F(ab')_2$ fragments, and possible even Fc fragments.

Aggregation or cross-linking of antibodies may be accomplished by any known method, such as heat or chemical aggregation. Any level of aggregation or cross-linking may be sufficient, although increased aggregation may result in increased fibrocyte suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

(vi) Interleukin-15 Antagonists

IL-15 antagonists encompassed by the present invention include a broad variety of molecules that antagonize or inhibit IL-15 activity (i.e., IL-15 mediated anti-apoptosis) including, but not limited to, anti-IL-15 antibodies, anti-IL-i 5R antibodies, soluble IL-15Rs, IL-15 muteins, anti-IL-15 small molecules and anti-IL-15R small molecules. Other antagonists, such as binding proteins and peptide mimetics, which are capable of inhibiting IL-15 activity, also are included. In a particular embodiment, the antagonist is capable of interfering with the assembly of the IL-15Rα, β, and γ subunits, e.g., the antagonist binds to an epitope located on the β- or γ-chain interacting domain of IL-15. In another particular embodiment, the antagonist is an IL-15 mutein, e.g., an IL-15 mutant that is capable of binding to IL-15Rα (but is not able to bind to either or both of the β- and/or γ-subunits of IL-15R and, therefore, is not able to effect signaling.

B. Profibrotic Factor Antagonists

Another component of the subject conjoint therapies agents that inhibit or antagonize of profibrotic factors, such as agents that antagonize one or more growth factors or cytokines involved in the formation and maintenance of fibrotic tissue. In this manner, compositions and methods of the present invention target both fibrocyte differentiation and fibrotic tissue formation and maintenance as part of a combined treatment.

Profibrotic factors that may be targeted with antagonists as part of the therapies of the to present invention include, without limitation, a growth factor type β (TGF-β, including TGF-(β1-5), VEGF, EGF, PDGF, IGF, RANTES, members of the interleukin family (e.g., IL-1, IL-4, IL-5, IL-6, IL-8 and IL-13), tumor necrosis factor type alpha (TNF-α), platelet-derived growth factor (PDGF), basic fibroblast growth factor (bFGF), monocyte chemoattractant protein type 1 (MCP-1), macrophage inflammatory protein (e.g., MIP-1α, MIP-2), connective tissue growth factor (CTGF), endothelin-1, angiotensin-II, leptin, chemokines (e.g., CCL2, CCL12, CXCL12, CXCR4, CCR3, CCR5, CCR7, SLC/CCL21), integrins (e.g., α1β1, α2β1 αvβ6, αvβ3), tissue inhibitors of matrix metalloproteinases (e.g., TIMP-1, TIMP-2) and other factors known to promote or be related to the formation, growth, or maintenance of fibrotic tissue. The present invention may include compositions or methods that target one or more of the foregoing factors and cytokines.

In certain embodiments, a suitable component of the composition may include antibodies directed to one or more of the profibrotic factors. Such antibodies may be purified, unpurified, or partially purified. The antibodies may be polyclonal or monoclonal antibodies, derived from any suitable animal source, such as mouse, rabbit, rat, human, horse, goat, bovine, and the like. Such antibodies may include antibody fragments, single chain antibodies, polymerized antibodies and/or antibody fragments, and the like.

In certain embodiments, a suitable composition may include antagonists of the corresponding receptor of one or more of the profibrotic factors. Such antagonists may include inactive forms of one or more of the profibrotic factors and/or cytokines, such as fragments thereof. Such forms in suitable concentrations may compete with its corresponding profibrotic factors and/or cytokines for binding to its receptor.

Similarly, certain antibodies to the receptor may be used to interfere with or prevent binding thereto of the corresponding profibrotic factors and/or cytokines.

In other selected embodiments, compositions of the present invention may include soluble forms of the receptor of one or more of the profibrotic factors and/or cytokines, such that the soluble receptor competes with its corresponding native cellular receptor for the target ligand.

In other selected embodiments, suitable components of the composition may include compounds that compete with or otherwise interfere with binding of one or more of the profibrotic factors and/or cytokines with its receptor. For example, the proteoglycan decorin is known to bind to TGF-β, thereby reducing its availability for binding to its receptor. Mannose-6-phospate is also known to compete with TGF-β for binding to its corresponding receptor. Other known binding inhibitors of TGF-β include latent transforming growth factor-β binding protein (LTBP) and latency associated peptide (LAP), both of which natively binding to the intracellular precursor of TGF-β.

In certain embodiments, a suitable component of the composition may include one or more oligoribonucleotides that contain at least one sequence that is antisense with respect to one or more of the profibrotic factors and/or cytokines. Such components may also include one or more expression plasmids having suitable transcriptional control sequences that yield antisense sequences. In other selected embodiments of the present invention, a suitable component may include one or more double-stranded oligoribonucleotides, or expression plasmids encoding thereof, that are suitable for degrading transcripts of one or more of the profibrotic factors and/or cytokines via RNA-mediated interference.

A suitable profibrotic factor antagonist of the composition may include components known to inhibit, attenuate, or interfere with one or more components of the intracellular signaling pathways activated by one or more of the profibrotic factors upon binding to its corresponding receptor.

For example, a composition of the present invention may include components that inhibit or attenuate downstream signal pathway molecules such as SMAD family members and SARA.

A suitable component of the composition may include one or more molecules that are suitable for inhibiting or interfering with the cellular adhesions require for fibrosis. For example, a suitable component may include interfering antibodies to the ICAM-1 and/or CD11 molecules, the extracellular matrix and/or α1β1 integrin, the extracellular matrix and/or α2β1 integrin, thereby interfering with the adhesion interaction there between.

In other selected embodiments, a suitable profibrotic factor antagonist may include inhibitors of collagen synthesis, such as proline analogs that interfere with post-translation processing of collagen precursors. Pirfenidone, for example, is an orally active small molecule drug that may inhibit collagen synthesis, down regulate production of multiple cytokines and block fibroblast proliferation.

a. TGF-β Antagonists

Cytokines of the transforming growth factor (TGF) beta family play a central role in wound healing and in tissue repair, and are found in all tissues. TGF-β is produced by many parenchymal cell types, as well as infiltrating cells such as lymphocytes, monocytes/macrophages, and platelets. Following wounding or inflammation, such cells such are potential sources of TGF-β. In general, TGF-β stimulates the production of various extracellular matrix proteins, inhibits the degradation of these matrix proteins, and promotes tissue fibrosis, all of which contribute to the repair and restoration of the affected tissue. In many diseases, excessive TGF-β contributes to a pathologic excess of tissue fibrosis that can compromise normal organ function.

The term "TGF-β" as used herein includes TGF-β1, TGFβ2, TGF-β3, TGF-β4 and TGF-β5. Also included are other related proteins with similar properties.

As used herein, a "TGF-β antagonist" is any molecule that is able to decrease the amount or activity of TGF-β, either within a cell or within a physiological system. Preferably, the TGF-β antagonist acts to decrease the amount or activity of a TGF-β 1, 2, or 3. For example, a TGF-β antagonist may be a molecule that inhibits expression of TGF-β at the level of transcription, translation, processing, or transport; it may affect the stability of TGF-β or conversion of the precursor molecule to the active, mature form; it may affect the ability of TGF-β to bind to one or more cellular receptors (e.g., Type I, II or III); or it may interfere with TGF-β signaling.

A variety of TGF-β antagonists and methods for their production are known in the art and many more are currently under development. The specific TGF-β antagonist employed is not a limiting feature; any effective TGF-β antagonist as defined herein may be useful in the methods and compositions of this invention. Preferably, the TGF-β antagonist is a TGF-β1, TGF-β2, or TGF-β3 antagonist. Most preferably the antagonist is a TGF-β1 antagonist.

Examples of TGF-β antagonists include, but are not limited to: monoclonal and polyclonal antibodies directed against one or more isoforms of TGF-β (Dasch et al., U.S. Pat. No. 5,571,714; see, also, WO 97/13844 and WO 00/66631); TGF-β receptors, soluble forms of such receptors (preferably soluble TGF-β type III receptor), or antibodies directed against TGF-β receptors (Segarini et al., U.S. Pat. No. 5,693,607; Lin et al., U.S. Pat. No. 6,001,969, U.S. Pat. No. 6,010,872, U.S. Pat. No. 6,086,867, U.S. Pat. No. 6,201,108; WO 98/48024; WO 95/10610; WO 93/09228; WO 92/00330); latency associated peptide (WO 91/08291); large latent TGF-β (WO 94/09812); fetuin (U.S. Pat. No. 5,821,227); decorin and other proteoglycans such as biglycan, fibromodulin, lumican and endoglin (WO 91/10727; Ruoslahti et al., U.S. Pat. No. 5,654,270, U.S. Pat. No. 5,705,609, U.S. Pat. No. 5,726,149; Border, U.S. Pat. No. 5,824,655; WO 91/04748; Letarte et al., U.S. Pat. No. 5,830,847, U.S. Pat. No. 6,015,693; WO 91/10727; WO 93/09800; and WO 94/10187); somatostatin (WO 98/08529); mannose-6-phosphate or mannose-1-phosphate (Ferguson, U.S. Pat. No. 5,520,926); prolactin (WO 97/40848); insulin-like growth factor II (WO 98/17304); IP-10 (WO 97/00691); arg-gly-asp containing peptides (Pfeffer, U.S. Pat. No. 5,958,411; WO 93/10808); extracts of plants, fungi and bacteria (EP-A-813 875; JP 8119984; and Matsunaga et al., U.S. Pat. No. 5,693,610); antisense oligonucleotides (Chung, U.S. Pat. No. 5,683,988; Fakhrai et al., U.S. Pat. No. 5,772,995; Dzau, U.S. Pat. No. 5,821,234, U.S. Pat. No. 5,869,462; and WO 94/25588); proteins involved in TGF-β signaling, including SMADs and MADs (EP-A-874 046; WO 97/31020; WO 97/38729; WO 98/03663; WO 98/07735; WO 98/07849; WO 98/45467; WO 98/53068; WO 98/55512; WO 98/56913; WO 98/53830; WO 99/50296; Falb, U.S. Pat. No. 5,834,248; Falb et al., U.S. Pat. No. 5,807,708; and Gimeno et al., U.S. Pat. No. 5,948,639), Ski and Sno (Vogel, 1999, Science, 286:665; and Stroschein et al., 1999, Science, 286:771-774); and any mutants, fragments or derivatives of the above-identified molecules that retain the ability to inhibit the activity of TGF-β.

In certain preferred embodiments, the TGF-β antagonist is a human or humanized monoclonal antibody that blocks TGF-β binding to its receptor (or fragments thereof such as F(ab)$_2$ fragments, Fv fragments, single chain antibodies and other forms or fragments of antibodies that retain the ability to bind to TGF-β. A preferred monoclonal antibody is a human or humanized form of the munne monoclonal antibody obtained from hybridoma 1D11.16 (ATCC Accession No. HB 9849 described in Dasch et al., U.S. Pat. No. 5,783,185).

TGF-β receptors and TGF-β-binding fragments of TGF-β receptors, especially soluble fragments are useful TGF-β antagonists in the methods of the present invention. In certain embodiments, the preferred inhibitor of TGF-β function is a soluble TGF-β receptor, especially TGF-β type II receptor (TGFBIIR) or TGF-β type III receptor (TGFBIIIR, or betaglycan) comprising, e.g., the extracellular domain of TGF-BIIR or TGFBIIIR, most preferably a recombinant soluble TGF-β receptor (rsTGFBIIR or rsTGFBIIIR). TGF-β receptors and TGF-β-binding fragments of TGF-β receptors, especially soluble fragments are useful TGF-β antagonists in the methods of the present invention. TGF-β receptors and the nucleic acids encoding them are well known in the art. The nucleic acid sequence encoding TGF-β type 1 receptor is disclosed in GENBank accession number L15436 and in U.S. Pat. No. 5,538,892 of Donahoe et al. The nucleic acid sequence of TGF-β type 2 receptor is publicly available under GENBank accession numbers AW236001; AI35790; AI279872; AI074706; and AA808255. The nucleic acid sequence of TGF-β type 3 receptor is also publicly available under GENBank accession numbers NM 003243; AI887852; AI817295; and AI681599.

Suitable TGF-β antagonists for use in the present invention will also include functional mutants, variants, derivatives and analogues of the aforementioned TGF-β antagonists, so long as their ability to inhibit TGF-β amount or activity is retained. As used herein, "mutants, variants, derivatives and analogues" refer to molecules with similar shape or structure to the parent compound and that retain the ability to act as TGF-β antagonists. For example, any of the TGF-β antagonists disclosed herein may be crystallized, and useful analogues may be rationally designed based on the coordinates responsible for the shape of the active site(s). Alternatively, the ordinarily skilled artisan may, without undue experimentation, modify the functional groups of a known antagonist and screen such modified molecules for increased activity, half-life, bioavailability or other desirable characteristics. Where the TGF-β antagonist is a polypeptide, fragments and modifications of the polypeptide may be produced to increase the ease of delivery, activity, half-life, etc (for example, humanized antibodies or functional antibody fragments, as discussed above). Given the level of skill in the art of synthetic and recombinant polypeptide production, such modifications may be achieved without undue experimentation. Persons skilled in the art may also design novel inhibitors based on the crystal structure and/or knowledge of the active sites of the TGF-β inhibitors described herein.

Polypeptide inhibitors such as the soluble TGF-β receptors may also be effectively introduced via gene transfer. Accordingly, certain embodiment of the present method involve the use of a vector suitable for expression of a TGF-β receptor or binding partner, preferably a soluble receptor or binding partner. In certain preferred embodiments, administration of a soluble TGF-β antagonist can be effected by gene transfer using a vector comprising cDNA encoding the soluble antagonist, most preferably cDNA encoding the extracellular domain of TGF-β type II (rsTGFBIIR) or type III receptor (rsTGFBIIIR), which vector is administered, preferably topically, to a donor organ to cause in situ expression of the soluble TGF-β antagonist in cells of the organ transfected with the vector. Such in situ expression inhibits the activity of TGF-β and curbs TGF-β-mediated fibrogenesis. Any suitable vector may be used. Preferred vectors include adenovirus, lenti virus, Epstein Barr virus (EBV), adeno associated virus (AAV), and retroviral vectors that have been developed for the purpose of gene transfer. Other, non-vector methods of gene transfer may also be used, for example, lipid/DNA complexes, protein/DNA conjugates, naked DNA transfer methods, and the like.

Additional suitable TGF-β antagonists developed for delivery via adenoviral gene transfer include, but are not limited to: a chimeric cDNA encoding an extracellular domain of the TGF-β type II Receptor fused to the Ig Fc domain (Isaka et al., 1999, *Kidney Int.*, 55:465-475), adenovirus gene transfer vector of a dominant-negative mutant of TGF-β type II Receptor (Zhao et al, 1998, *Mech. Dev.*, 72:89-100.), and an adenovirus gene transfer vector for decorin, a TGF-β binding proteoglycan (Zhao et al., 1999, *Am. J. Physiol.*, 277:L412-L422). Adenoviral-mediated gene transfer is very high efficiency compared to other gene delivering modalities.

C. Anti-Fibrotic Agents

In certain embodiments, the profibrotic factor antagonists can be replaced with, or augmented with, a cytokine known to have anti-fibrotic effects, such as IFN-γ, BMP-7, HGF or IL-10.

The nucleic acid sequences encoding IFN-γ polypeptides may be accessed from public databases, e.g. Genbank, journal publications, etc. While various mammalian IFN-γ polypeptides are of interest, for the treatment of human disease, generally the human protein will be used. Human IFN-γ coding sequence may be found in Genbank, accession numbers X13274; V00543; and NM000619. The corresponding genomic sequence may be found in Genbank, accession numbers J00219; M37265; and V00536. See, for example. Gray et al. (1982) Nature 295:501 (Genbank X13274); and Rinderknecht et al. (1984) J. Biol. Chem. 259:6790.

IFN-γ1b (Actimmune™; human interferon) is a single-chain polypeptide of 140 amino acids. It is made recombinantly in *E. coli* and is unglycosylated. Rinderknecht et al. (1984) J. Biol. Chem. 259:6790-6797.

The IFN-γ to be used in the compositions of the present invention may be any of natural IFN-γs, recombinant IFN-γs and the derivatives thereof so far as they have a IFN-γ activity, particularly human IFN-γ activity. Although IFN-γ is based on the sequences as provided above, the production of the protein and proteolytic processing can result in processing variants thereof. The unprocessed sequence provided by Gray et al., supra. consists of 166 amino acids (aa). Although the recombinant IFN-γ produced in *E. coli* was originally believed to be 146 amino acids, (commencing at amino acid 20) it was subsequently found that native human IFN-γ is cleaved after residue 23, to produce a 143 aa protein, or 144 aa if the terminal methionine is present, as required for expression in bacteria During purification, the mature protein can additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG which, in the particular case of *E. coli* expression is not processed away. In other microbial systems or eukaryotic expression systems, methionine may be removed.

For use in the subject methods, any of the native IFN-γ peptides, modifications and variants thereof, or a combination of one or more peptides may be used which may have anti-fibrotic activity. IFN-γ peptides of interest include fragments, and can be variously truncated at the carboxy terminal end relative to the full sequence. Such fragments continue to exhibit the characteristic properties of human gamma interferon, so long as amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925, herein incorporated by reference. Native IFN-γ moieties include molecules variously extending from amino acid residues 24-150; 24-151, 24-152; 24-153, 24-155; and 24-157. Any of these variants, and other variants known in the art and having IFN-γ activity, may be used in the present methods.

The sequence of the IFN-γ polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. In one embodiment, the invention contemplates the use of IFN-γ variants with one or more non-naturally occurring glycosylation and/or pegylation sites that are engineered to provide glycosyl- and/or PEG-derivatized polypeptides with reduced serum clearance, such as the IFN-γ polypeptide variants described in International Patent Publication No. WO01/36001. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

In other embodiments the anti-fibrotic agent can be an HGF agonists. Examples include, but are not limited to, Refanalin (Angion Biomedica).

In still other embodiments, the antifibrotic agent can be a calcium channel blocker, such as verapamil. Such agents can have an antifibrotic effect due not only to their ability to diminish the synthesis of collagen type I, but also as a consequence to stimulating the degradation of collagen type I fibers. In vitro studies of fibroblasts show that the extracellular transport of collagen depends on the presence of calcium. Verapamil, a calcium-channel blocker, reduces intracellular the calcium concentration and increases collagenase activity. It also inhibits the proliferation of fibroblasts.

In still other embodiments, the antifibrotic agent can be an ACE (Angiotensin-Converting Enzyme) inhibitor such as alacepril, benazepril, captopril, cilazapril, ceranapril, delapril, enalapril, enalaprilat, fosinopril, fosinoprilat, imidapril, lisinopril, moexipril, perindopril, perindoprilat, quinapril, quinaprilat, ramipril, saralasin acetate, spirapril, temocapril, trandolapril, fasidotrilat, beclometasone dipropionate, FPL-66564, idrapril, MDL-100240, and S-5590.

In other embodiments, the antifibrotic agent can be an angiotensin receptor antagonist, such as candesartan, irbesartan, losartan, valsartan, telmisartan, or eprosartan.

In other embodiments, the antifibrotic agent can be an inhibitor of the VEGF signaling pathway. Exemplary VEGF receptor antagonists include inhibitors of a VEGF (e.g., VEGF-A, -B, or -C), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B), VEGFR3 antibodies such as mF4-31C1 from Imclone Systems, modulators of VEGFR expression (e.g., VEGFR1 expression modulator Sirna-027) or inhibitors of VEGF receptor downstream signaling.

Exemplary inhibitors of VEGF include bevacizumab, pegaptanib, ranibizumab, NEOVASTAT™, AE-941, VEGF Trap, and PI-88.

Exemplary VEGF receptor antagonists include inhibitors of VEGF receptor tyrosine kinase activity. 4-[4-(1-Amino-1-methylethyl)phenyl]-2-[4-(2-morpholin-4-yl-ethyl)phenylam-ino]pyrimidine-5-carbonitrile (JNJ-17029259) is one of a structural class of 5-cyanopyrimidines that are orally available, selective, nanomolar inhibitors of the vascular endothelial growth factor receptor-2 (VEGF-R2). Additional examples include: PTK-787/ZK222584 (Astra-Zeneca), SU5416, SU11248 (Pfizer), and ZD6474 ([N-(4-bromo-2-fluorophenyl)-6-methoxy-7-[(1-methylpiperidin-4-yl)methoxy-]quinazolin-4-amine]), vandetanib, cediranib, AG-013958, CP-547632, E-7080, XL-184, L-21649, and ZK-304709. Other VEGF antagonist agents are broad specificity tyrosine kinase inhibitors, e.g., SU6668 (see, e.g., Bergers, B. et al., 2003 J. Clin. Invest. 111:1287-95), sorafenib, sunitinib, pazopanib, vatalanib, AEE-788, AMG-706, axitinib, BIBF-1120, SU-14813, XL-647, XL-999, ABT-869, BAY-57-9352, BAY-73-4506, BMS-582664, CEP-7055, CHIR-265, OSI-930, and TKI-258. Also useful are agents that down regulate VEGF receptors on the cell surface, such as fenretinide, and agents which inhibit VEGF receptor downstream signaling, such as squalamine.

In other embodiments, the antifibrotic agent can be a kinase inhibitor. Examples of MEK inhibitors include, but are not limited to, PD325901, ARRY-142886, ARRY-438162 and PD98059. Examples of EGFR inhibitors include, but are not limited to, Iressa™ (gefitinib, AstraZeneca), Tarceva™ (erlotinib or OSI-774, OSI Pharmaceuticals Inc.), Erbitux™ (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Examples of ErbB2 receptor inhibitors include, but are not limited to, CP-724-714, CI-1033 (canertinib), Herceptin™ (trastuzumab), Omnitarg™ (2C4, petuzumab), TAK-165, GW-572016 (Ionafarnib), GW-282974, EKB-569, PI-166, dHER2 (HER2 Vaccine), APC8024 (HER2 Vaccine), anti-HER/2neu bispecific antibody, B7.her2IgG3, AS HER2 tri functional bispecfic antibodies, mAB AR-209 and mAB 2B-1. Specific IGFIR antibodies that can be used in the present invention include those described in International Patent Application No. WO 2002/053596 that is herein incorporated by reference in its entirety. Examples of PDGFR inhibitors include, but are not limited to, SU9518, CP-673,451 and CP-868596. Examples of AXL inhibitors include, but are not limited to, SGI-AXL-277 (SuperGen) as well as inhibitors disclosed in U.S. Pat. Pub. 20050186571. Examples of FGFR inhibitors include, but are not limited to, PD 17034, PD166866, and SU5402. Examples of TIE2 inhibitors include, but are not limited to, those described in Kissau, L. et. al., J Med Chem, 46:2917-2931 (2003).

Kinase inhibitors also encompass inhibitors with multiple targets. Pan ERBB receptor inhibitors include, but are not limited to, GW572016, CI-1033, EKB-569, and Omnitarg. MP371 (SuperGen) is an inhibitor of c-Kit, Ret, PDGFR, and Lck, as well as the non-receptor tyrosine kinase c-src. MP470 (SuperGen) is an inhibitor of c-Kit, PDGFR, and c-Met. Imatinib (Gleevec™) is an inhibitor of c-kit, PDGFR, and ROR, as well as the non-receptor tyrosine kinase bcl/abl. Lapatinib (Tykerb™) is an epidermal growth factor receptor (EGFR) and ERBB2 (Her2/neu) dual tyrosine kinase inhibitor. Inhibitors of PDGFR and VEGFR include, but are not limited to, Nexavar™ (sorafenib, BAY43-9006), Sutent™ (sunitinib, SU11248), and ABT-869. Zactima™ (vandetanib, ZD-6474) is an inhibitor of VEGFR and EGFR. In other embodiments the anti-fibrotic agent can be an anti-oxidant. Examples include, but are not limited to, Heptax (Hawaii Biotech), N-acetylcysteine (Pierre Fabre), tocopherol, silimarin and Sho-saiko-To (H-09).

In other embodiments the anti-fibrotic agent can be inhibitors of collagen expression. Examples include, but are not limited to Pirfenidone (InterMune), Halofuginone (Collgard) and F351 (Shanghai Genomics).

In other embodiments the anti-fibrotic agent can be an peroxisome proliferative activated receptor (PPAR) gamma agonists. Examples include, but are not limited to, farglitizar (GSK), pioglitazone (Takeda), rosiglitazone (GSK).

In other embodiments the anti-fibrotic agent can be an Farnesoid X receptor agonists. Examples include, but are not limited to, INT-747 (Intercept Pharmaceuticals).

In other embodiments the anti-fibrotic agent can be an caspase inhibitors. Examples include, but are not limited to, PF-3491390 (Pfizer, formally IDN-6556), and LB84318 (LG Life Sciences).

In other embodiments the anti-fibrotic agent can be an inhibitors of advanced glycation endproducts (AGEs) or their receptors such as RAGE. Examples of AGE inhibitors include, but are not limited to, Pyridoxamine (Biostratum). Examples of RAGE inhibitors include, but are not limited to, TTP-488 (Transtech Pharma) and TTP-4000 (Transtech Pharma).

In other embodiments the anti-fibrotic agent can be a LMW heparin or heparin analog. Examples include, but are not limited to, Sulodexide (Keryx).

In other embodiments the anti-fibrotic agent can be a protein kinase C (PKC) inhibitor. Examples include, but are not limited to, Ruboxistaurin mesilate hydrate (Lilly).

In other embodiments the anti-fibrotic agent can be a ADAM-10 inhibitor. Examples include, but are not limited to, XL-784 (Exelixis).

In other embodiments the anti-fibrotic agent can be a copper chelator. Examples include, but are not limited to, Trientine (Protemix), Coprexa (Pipex).

In other embodiments the anti-fibrotic agent can be a rho kinase inhibitor. Examples include, but are not limited to, SLx-2119 and SLx-3060 (Surface Logix).

D. Exemplary Conditions for Treatment

Fibrosis is generally characterized by the pathologic or excessive accumulation of collagenous connective tissue. Fibrotic disorders that may be amenable to treatment with the subject method include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport's syndrome, HIV-associated nephropathy, polycystic kidney disease, Fabry's disease, diabetic nephropathy, chronic glomerulonephritis, nephritis associated with systemic lupus, and the like), cutis keloid formation, progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's opthalmopathy, diabetic retinopathy, glaucoma, Peyronie's disease, penis fibrosis, urethrostenosis after the test using a cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), fibrosis induced by chemical or environmental insult (e.g., cancer chemotherapy, pesticides, radiation (e.g., cancer radiotherapy), and the like), and the like.

Compositions may be applied locally or systemically. The compositions may also be supplied in combinations or with cofactors. Compositions may be administered in an amount sufficient to restore normal levels, if the composition is normally present in the target location, or they may be administered in an amount to raise levels above normal levels in the target location.

The compositions of the present invention may be supplied to a target location from an exogenous source, or they may be made in vivo by cells in the target location or cells in the same organism as the target location.

Compositions of the present invention may be in any physiologically appropriate formulation. They may be administered to an organism by injection, topically, by inhalation, orally or by any other effective means.

The same compositions and methodologies described above to suppress or inhibit excessive fibrosis formation and maintenance may also be used to suppress or inhibit inappropriate fibrosis formation. For example, they may treat or prevent a condition occurring in the liver, kidney, lung, heart and pericardium, eye, skin, mouth, pancreas, gastrointestinal tract, brain, breast, bone marrow, bone, genitourinary, a tumor, or a wound.

Generally, they may treat or prevent fibrosis resulting from conditions including but not limited to rheumatoid arthritis, lupus, pathogenic fibrosis, fibrosing disease, fibrotic lesions such as those formed after *Schistosoma japonicum* infection, radiation damage, autoimmune diseases, lyme disease, chemotherapy induced fibrosis, HIV or infection-induced focal sclerosis, failed back syndrome due to spinal surgery scarring, abdominal adhesion post surgery scarring, and fibrocystic formations.

Specifically, in the liver, they may treat or prevent fibrosis resulting from conditions including but not limited to alcohol, drug, and/or chemically induced cirrhosis, ischemia-reperfusion, injury after hepatic transplant, necrotizing hepatitis, hepatitis B, hepatitis C, primary biliary cirrhosis, and primary sclerosing cholangitis.

Relating to the kidney, they may treat or prevent fibrosis resulting from conditions including but not limited to proliferative and sclerosing glomerulonephritis, nephrogenic fibrosing dermopathy, diabetic nephropathy, renal tubulointerstitial fibrosis, and focal segmental glomerulosclerosis.

Relating to the lung, they may treat or prevent fibrosis resulting from conditions including but not limited to pulmonary interstitial fibrosis, drug-induced sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, and emphysema.

Relating to the heart and/or pericardium, they may treat or prevent fibrosis resulting from conditions including but not limited to myocardial fibrosis, atherosclerosis, coronary artery restenosis, congestive cardiomyopathy, heart failure, and other post-ischemic conditions.

Relating to the eye, they may treat or prevent fibrosis resulting from conditions including but not limited to exophthalmos of Grave's disease, proliferative vitroretinopathy, anterior capsule cataract, acute macular degeneration, corneal fibrosis, corneal scarring due to surgery, trabeculectomy-induced fibrosis, and other eye fibrosis.

Relating to the skin, they may treat or prevent fibrosis resulting from conditions including but not limited to Depuytren's contracture, scleroderma, keloid scarring, psoriasis, hypertrophic scarring due to burns, atherosclerosis, restenosis, and psuedoscleroderma caused by spinal cord injury.

Relating to the mouth, they may treat or prevent fibrosis resulting from conditions including but not limited to periodontal disease scarring and gingival hypertrophy secondary to drugs.

Relating to the pancreas, they may treat or prevent fibrosis resulting from conditions including but not limited to pancreatic fibrosis, stromal remodeling pancreatitis, and stromal fibrosis.

Relating to the gastrointestinal tract, they may treat or prevent fibrosis resulting from conditions including but not limited to collagenous colitis, villous atrophy, cryp hyperplasia, polyp formation, fibrosis of Chron's disease, and healing gastric ulcer.

Relating to the brain, they may treat or prevent fibrosis resulting from conditions including but not limited to glial scar tissue.

Relating to the breast, they may treat or prevent fibrosis resulting from conditions including but not limited to fibrocystic disease and desmoplastic reaction to breast cancer.

Relating to the bone marrow, they may treat or prevent fibrosis resulting from conditions including but not limited to fibrosis in myelodysplasia and neoplastic diseases.

Relating to the bone, they may treat or prevent fibrosis resulting from conditions including but not limited to rheumatoid pannus formation.

Relating to the genitourinary system, they may treat or prevent fibrosis resulting from conditions including but not limited to endometriosis, uterine fibroids, and ovarian fibroids.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

(i) Methods of Treating Idiopathic Pulmonary Fibrosis

The present invention provides methods of treating idiopathic pulmonary fibrosis to (IPF). The methods generally involve administering to an individual having IPF a combination of an effective amount of fibrocyte suppressor and an effective amount profibrotic cytokine antagonist.

In some embodiments, the dosing and efficacy of the treatment can be monitored by reversal or slowing of progressing of usual interstitial pneumonia (UIP) on histopathological evaluation of lung tissue obtained by surgical biopsy. The criteria for a diagnosis of IPF are known. Ryu et al. (1998) *Mayo Clin. Proc.* 73:1085-1101.

In other embodiments, a diagnosis of IPF is a definite or probable IPF made by high resolution computer tomography (HRCT). In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met.

In certain preferred embodiments, the subject combination therapy results in an increase, such as a statistically significant increase, in pulmonary function. Pulmonary function values are well known in the art. The following is an example of pulmonary function values that may be used. Other pulmonary function values, or combinations thereof, are intended to be within the scope of this invention. The values include, but are not limited to, FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity). FEV measures the volume of air exhaled over a pre-determined period of time by a forced expiration immediately after a full inspiration. FVC measures the total volume of air exhaled immediately after a full inspiration. Forced expiratory flow measures the volume of air exhaled during a FVC divided by the time in seconds. Vmax is the maximum flow measured during FVC. PEFR measures the maximum flow rate during a forced exhale starting from full inspiration. RV is the volume of air remaining in the lungs after a full expiration.

(ii) Methods of Treating Liver Fibrosis

The present invention provides methods of treating liver fibrosis, including reducing clinical liver fibrosis, reducing the likelihood that liver fibrosis will occur, and reducing a parameter associated with liver fibrosis. Of particular interest in many embodiments is treatment of humans.

Liver fibrosis is a precursor to the complications associated with liver cirrhosis, such as portal hypertension, progressive liver insufficiency, and hepatocellular carcinoma. A reduction in liver fibrosis thus reduces the incidence of such complications. Accordingly, the present invention further provides methods of reducing the likelihood that an individual will develop complications associated with cirrhosis of the liver by conjoint therapy involving the administration of fibrocyte suppressors and profibrotic cytokine antagonists. Whether treatment with a combination of fibrocyte suppressor and profibrotic cytokine antagonist is effective in reducing liver fibrosis is determined by any of a number of well-established techniques for measuring liver fibrosis and liver function. Whether liver fibrosis is reduced is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) *Hepatol.* 31:241-246; and METAVIR (1994) *Hepatology* 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: I, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) *J. Hepatol.* 13:372.

The Ishak scoring system is described in Ishak (1995) *J. Hepatol.* 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite. The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

(iii) Methods of Treating Renal Fibrosis

Renal fibrosis is characterized by the excessive accumulation of extracellular matrix (ECM) components. Overproduction of TGF-β is believed to underly tissue fibrosis caused by excess deposition of ECM, resulting in disease. TGF-β's fibrogenic action results from simultaneous stimulation of matrix protein synthesis, inhibition of matrix degradation and enhanced integrin expression that facilitates ECM assembly.

The present invention provides methods of treating renal fibrosis. The methods to generally involve administering to an individual having renal fibrosis a combination of fibrocyte suppressor and profibrotic cytokine antagonist. As used herein, an "effective amount" of a fibrocyte suppressor in combination with an "effective amount" of a profibrotic cytokine antagonist is a combined dosage that is effective in reducing renal fibrosis; and/or that is effective in reducing the likelihood that an individual will develop renal fibrosis; and/or that is effective in reducing a parameter associated with renal fibrosis; and/or that is effective in reducing a disorder associated with fibrosis of the kidney.

In one embodiment, an effective combination of fibrocyte suppressor and profibrotic cytokine antagonist is a combination that is sufficient to reduce renal fibrosis by at least about 10%, at least about 15%, at least about 20%, at least about 25%, at least about 30%, at least about 35%, at least about 40%, at least about 45%, at least about 50%, compared to the degree of renal fibrosis in the individual prior to treatment with the combination therapy of the present invention.

Whether fibrosis is reduced in the kidney is determined using any known method. For example, histochemical analysis of kidney biopsy samples for the extent of ECM deposition and/or fibrosis is performed. Other methods are known in the art. See, e.g., Masseroli et al. (1998) Lab. Invest. 78:511-522; U.S. Pat. No. 6,214,542.

In some embodiments, an effective combination of fibrocyte suppressor and profibrotic cytokine antagonist is that combination that is effective to increase kidney function by at least about 10%, at least about 15%, at least about 20%, at least about 25%, at least about 30%, at least about 35%, at least about 40%, at least about 45%, at least about 50%, compared to the basal level of kidney function in the individual prior to treatment with the combination therapy of the present invention.

In some embodiments, an effective combination of fibrocyte suppressor and profibrotic cytokine antagonist is that combination that is effective to slow the decline in kidney function by at least about 10%, at least about 15%, at least about 20%, at least about 25%, at least about 30%, at least about 35%, at least about 40%, at least about 45%, at least about 50%, compared to the decline in kidney function that would occur in the absence of treatment with the combination therapy of the present invention.

Kidney function can be measured using any known assay, including, but not limited to, plasma creatinine level (where normal levels are generally in a range of from about 0.6 to about 1.2 mg/dL); creatinine clearance (where the normal range for creatinine clearance is from about 97 to about 137 mL/minute in men, and from about 88 to about 128 mL/minute in women); the glomerular filtration rate (either calculated or obtained from inulin clearance or other methods), blood urea nitrogen (where the normal range is from about 7 to about 20 mg/dL); and urine protein levels.

The invention also provides a method for treatment of renal fibrosis in an individual comprising administering to the individual a combination of fibrocyte suppressor and profibrotic cytokine antagonist that is effective for prophylaxis or therapy of renal fibrosis in the individual, e.g., increasing the time to doubling of serum creatinine levels, increasing the time to end-stage renal disease requiring renal replacement therapy (e.g., dialysis or transplant), increasing the probability of survival, reducing the risk of death, ameliorating the disease burden or slowing the progression of disease in the individual, while reducing the incidence or severity of one or more side effects that would ordinarily arise from treatment with an effective amount of the fibrocyte suppressor or profibrotic cytokine antagonist alone.

(iv) Exemplary Drug Doses

| DRUG | DOSE | INDICATION | REFERENCE |
|---|---|---|---|
| Pirfenidone | 40 mg/kg | IPF | Nagai, S, Hamada, K., et al., Intern Med. (2002) 41(12): 1118-1123. |
| Pirfenidone | 50 mg/kg | IPF | Raghu, G., Johnson, WC., Lockhart, D., Mageto, Y., Am J. Respir. Crit Care Med., (1999) 159(4 Part 1): 1061-1069. |
| Gefitinib (anti EGFR antibody) | 200 mg/kg (mice) | Bleomycin lung model | Ishii, Y,. Fujimoto, S., Fukuda, T., Am J Respir Crit Care Med., (2006)Vol 174: 550-556. |
| AG1478 (Tyrphostin, EGF TI inhibitor) | 12 mg/kg | Bleomycin lung model | Ishii, Y,. Fujimoto, S., Fukuda, T., Am J Respir Crit Care Med., (2006)Vol 174: 550-556. |
| Imatinib mesylate (PDGFR/cAbl/cKit kinase inhibitor) | 50 mg/kg | Bleomycin lung model | Chaudhary, N., Schnapp, A., and Park, J., Am J Respir Crit Care Med., (2006)Vol 173: 769-776. |
| Anti TGF beta receptor antibody | 4 nmol | Bleomycin lung model | Wang, Q., Wang, Y., Hyde, DM., et al, Thorax (1999): 54: 805-812. |
| Losartan (angiotensin receptor antagonist) | 27 mg/kg | Bleomycin lung model | Yao, M., Zhu, J., Zhao, M., and Lu, Y., Respiration (2006): 73: 236-242. |

E. Exemplary Model Systems for Testing Drug Combinations (i) Bleomycin-Induced Lung Fibrosis Pulmonary fibrosis is produced in male Sprague-Dawley rats weighing 200-250 grams. An endotracheal dose (via transoral route) of 2.5-6.67 U/kg of bleomycin dissolved in 0.9% sodium chloride at a volume of 1.5 ml/kg is administered on Day 0. On study Days 1, 3, 5, 7 and 9, rats in the treated group are dosed intravenously via tail vein with 1.6 mg/kg of SAP at a dose volume of 1.3 mL/kg. Untreated rats are dosed with 1.3 mL/kg of saline. On Day 14 lung function is assessed by measuring blood oxygen saturation (pulse oximetry) and/or PO$_2$ (blood gas analyzer). The animals are then sacrificed, and the left lung is processed for total collagen content (Sircol assay) and the right lung is fixed in 10% formalin, sectioned and stained with Sirius Red and hematoxylin and eosin to assess collagen deposition. (See Cortijo, et al. Attenuation by oral N-acetylcystein of bleomycin-induced lung injury in rats. *Eur Respir J* 17:1228-1235, 2001)

In a combination treatment study, pulmonary fibrosis is induced in C57BL/6 mice (6-8 weeks of age) by the surgical intratracheal instillation of 0.05 U of bleomycin (Blenoxane, sterile bleomycin sulfate; Bristol-Meyers Pharmaceuticals, Evansville, Ind.) dissolved in PBS (approximately 1.7 U/kg) and termed as day 0. Groups are sacrificed and lung tissues analyzed at day 21 after bleomycin injection. Control mice will receive intratracheal PBS. For both the IFN-γ and anti-IL13 studies, mice received hSAP in a dosing schedule (5 or 20 mg/kg, ip. q2d for 5 doses starting on day 11).

For the IFN-γ combination study, mice receive bleomycin on day 0 and IFN-γ on days −1, 1 and 2 (im 10,000 U/mouse; see Table 2). The mice that do not receive IFN-γ but did receive hSAP (groups 4 and 5), were given saline intramuscularly on days −1, 1 and 2.

For the hSAP/anti-IL13 study, mice receive anti-IL13 (UMich reagent, 200 ug/dose, pAb, ip; see Table 3) on days 14, 16, 18 and 20 only.

Mice are killed with anesthetic overdose; blood is removed by cardiac puncture and collected into EDTA-containing tubes to allow for processing for plasma. Lungs are perfused via the left ventricle in situ with sterile PBS (approx 2-3 mL until adequate perfusion) then removed en bloc and flash frozen until being processed for protein analysis. Total soluble collagen is measured in lung homogenates using the hydroxyproline assay and analyzed histologically using Masson trichrome staining Table 2: Study design for hSAP/IFN-γ combination study in female C57Bl/6 mice.

| Group | Group Name | Intratracheal Challenge | hSAP (ip q2 d for 5 doses starting on day 11) | IFNγ (im qd −1, 1 and 2) |
|---|---|---|---|---|
| 1 | Control | PBS | No | No |
| 2 | Bleo Control | Bleomycin | HSA | No |
| 3 | Bleo + IFN Control | Bleomycin | HSA | IFNγ |
| 4 | Bleo + low SAP | Bleomycin | 5 mg/kg hSAP | Saline |
| 5 | Bleo + high SAP | Bleomycin | 20 mg/kg hSAP | Saline |
| 6 | Bleo + low IFN | Bleomycin | 5 mg/kg hSAP | IFNγ |
| 7 | Bleo + high IFN | Bleomycin | 20 mg/kg hSAP | IFNγ |

TABLE 3

Study design for hSAP/anti-IL13 combination study in male C57Bl/6 mice

| Group | Group Name | Intratracheal Challenge | hSAP (ip q2 d for 5 doses starting on day 11) | Anti-IL13 (200 ug ip, q2 d from day 14) |
|---|---|---|---|---|
| 1 | Control | PBS | No | No |
| 2 | Bleo Control | Bleomycin | Saline | No |
| 3 | Bleo + antiIL13 Control | Bleomycin | Saline | Yes |

TABLE 3-continued

Study design for hSAP/anti-IL13 combination study in male C57B1/6 mice

| Group | Group Name | Intratracheal Challenge | hSAP (ip q2 d for 5 doses starting on day 11) | Anti-IL13 (200 ug ip, q2 d from day 14) |
|---|---|---|---|---|
| 4 | Bleo + low SAP | Bleomycin | 5 mg/kg hSAP | No |
| 5 | Bleo + high SAP | Bleomycin | 20 mg/kg hSAP | No |
| 6 | Bleo + low antiIL13 | Bleomycin | 5 mg/kg hSAP | Yes |
| 7 | Bleo + high antiIL13 | Bleomycin | 20 mg/kg hSAP | Yes |

(ii) Liver Fibrosis, Carbon Tetrachloride Administration

Hepatic fibrosis is produced in male Wistar rats weighing 200-225 grams. On Day 0, rats receive an intragastric dose of $CCl_4$ in olive oil (0.08 mL $CCl_4$/mL of olive oil; initial dose of 412 mg $CCl_4$/kg) or olive oil alone (controls). Rats are dosed with $CCl_4$ twice a week for the duration of the study, with weekly doses adjusted based on body weight changes to reduce mortality. Treated rats are dosed IP with 1.6 mg/kg of SAP every other day beginning on Day 1; control rats are dosed with equal volumes of vehicle. On Day 24, rats are sacrificed, body and liver weights are assessed, and liver tissue is harvested for analysis. Total collagen content is measured with the Sircol assay, and collagen deposition is measured with Masson trichrome and Sirius red staining. Myrofibroblast activation is determined by immunostaining for α-SMA. (See Parsons C J, et al. Antifibrotic effects of a tissue inhibitor of metalloprotein-ase-1 antibody on established liver fibrosis in rats. *Hepatology* 40:1106-1115, 200 and Rivera C A, et al. Attenuation of $CCL_4$-induced hepatic fibrosis by $GdCl_3$ treatment or dietary glycine. *Am J Physiol Gastrointest Liver Physiol* 281:G200-G207, 2001)

(iii) Liver Fibrosis, Bile Duct Ligation

Liver injury is induced in adult male rats by ligation of the common bile duct on Day 0. Treated rats are dosed IP with 1.6 mg/kg of SAP every other day beginning on Day 1; control rats are dosed with equal volumes of vehicle. On Day 14, rats are sacrificed, body and liver weights are assessed, and liver tissue is harvested for analysis. Total collagen content is measured with the Sircol assay, and collagen deposition is measured with Masson trichrome and Sirius red staining. Myrofibroblast activation is determined by immunostaining for α-SMA. (See Kisseleva T, et al. Bone marrow-derived fibrocytes participate in pathogenesis of liver fibrosis. *J Hepatology* 45:429-438, 2006; Hellerbrand C, et al. Expression of intracellular adhesion molecule 1 by activated hepatic stellate cells. *Hepatology* 24:670-676, 1996; and Tramas E G, Symeonidis A. Morphologic and functional changes in the livers of rats after ligation and excision of the common bile duct. *Am J Pathol* 33:13-27, 1957)

(iv) UUO-Induced Renal Fibrosis

Unilateral Ureter Obstruction (UUO) in the rat is a suitable model of renal fibrosis'. Renal fibrosis was induced in Sprague Dawley rats weighing 200-250 grams. Rats were anesthetized with ketamine (100 mg/kg) and xylazine (5 mg/kg). All surgical procedures were conducted using aseptic techniques.

The left kidney, renal artery and vein were exposed and the ureter occluded using suture. The surgical site was then sutured closed.

Human serum albumin in PBS (group 1) or hSAP in PBS (groups 2-5) was given to animals by intravenous (iv) injection every other day from day 0 to day 12 as detailed in Table 4. Enalapril was be added to the drinking water of animals in groups 2, 5 and 6, beginning on the day of study and continuing until sacrifice (day 14).

On day 14, animals were sacrificed and both the left occluded and right contralateral control kidneys excised.

TABLE 4

Study design for UUO-induced renal fibrosis

| Group | Number of Animals | Treatment | Treatment Schedule of hSAP | Sacrifice Schedule | Volume |
|---|---|---|---|---|---|
| 1 | 6 Sprague Dawley males | HSA, ip, q2d | Days 0, 2, 4, 6, 8, 10 and 12. | day 14 | Adjust per body weight |
| 2 | 6 Sprague Dawley males | Enalapril in drinking water at 200 mg/L | Day −1 to 14 | day 14 | |
| 3 | 6 Sprague Dawley males | hSAP in PBS, iv, q2d, 2 mg/kg | Days 0, 2, 4, 6, 8, 10 and 12. | day 14 | Adjust per body weight |
| 4 | 6 Sprague Dawley males | hSAP in PBS, iv, q2d, 2 mg/kg Enalapril in drinking water at 200 mg/L | Days 0, 2, 4, 6, 8, 10 and 12. Day −1 to 14 | day 14 | Adjust per body weight |

(See M. El Chaar et al., Am J Physiol Renal Physiol 292, F1291 (April, 2007) and M. D. Burdick et al., Am J Respir Crit Care Med 171, 261 (Feb. 1, 2005))

To determine the extent of fibrosis induced by 14 days of UUO, kidney sections from all groups of animals were stained with Masson Trichrome and the extent of Trichrome positivity determined using image analysis (see FIG. 1). In the uninjured kidney, there was approximately 5% collagen deposition, whereas the injury mediated by UUO resulted in an increase in collagen deposition in the kidney in the HSA control treated animals (approximately 22% Trichrome staining). Either enalapril alone (approximately 15%) or 2 mg/kg hSAP alone (approximately 25%) did not statistically inhibit the increase in collagen deposition. However, there was a significant inhibition in Trichrome staining in the animals treated with the combination of enalapril and hSAP ($p<0.05$; approximately 10%). Moreover, the extent of collagen deposition in the animals treated with the combination of enalapril and hSAP was statistically attenuated in comparison to hSAP alone (p<0.01). Taken together these data indicate that the combination of enalapril+hSAP provides greater therapeutic activity in comparison to either enalapril alone or hSAP alone in a rat model of UUO-induced renal fibrosis.

The invention claimed is:

1. A method of treating fibrosis, the method comprising administering to a patient in need thereof a combination of a Serum Amyloid P (SAP) protein and enalapril.

2. The method of claim 1, wherein the SAP protein and enalapril are co-formulated.

3. The method of claim 1, wherein the SAP protein and enalapril are administered simultaneously.

4. The method of claim 1, wherein the SAP protein and enalapril are administered within a time of each other to produce overlapping therapeutic concentrations in the patient.

* * * * *